United States Patent [19]

Gratteau et al.

[11] Patent Number: 4,672,322
[45] Date of Patent: Jun. 9, 1987

[54] HIGH SENSITIVITY CONDUCTIVITY DETECTOR

[75] Inventors: Jack E. Gratteau, North Palm Beach, Fla.; Dennis W. Janzen, Woodcliff Lake, N.J.; Shailesh Atreya, Newport Beach, Calif.

[73] Assignee: Milton Roy Company, St. Petersburg, Fla.

[21] Appl. No.: 644,048

[22] Filed: Aug. 24, 1984

[51] Int. Cl.⁴ .............................................. G01N 27/04
[52] U.S. Cl. ..................... 324/441; 324/439; 324/443; 324/450; 340/870.38; 204/400; 204/406
[58] Field of Search ............... 324/438, 439, 441, 450, 324/62, 443, DIG. 1; 340/870.38, 870.39; 374/178, 163; 62/3; 204/400, 406

[56] References Cited

U.S. PATENT DOCUMENTS

| | | | |
|---|---|---|---|
| 3,197,697 | 7/1965 | McCauley | 324/62 |
| 3,421,982 | 1/1969 | Schultz | 324/439 |
| 3,441,490 | 4/1969 | Johansson | 324/439 |
| 3,946,309 | 3/1976 | Roughton | 324/439 |
| 4,035,719 | 7/1977 | Anderson | 324/441 |
| 4,066,365 | 1/1978 | Staunton | 62/3 |
| 4,262,665 | 12/1980 | Mate | 324/62 |
| 4,532,510 | 7/1985 | Bertrand | 324/62 |

OTHER PUBLICATIONS

D. T. Gjerde, J. S. Fritz, and G. Schmuckler, Anion Chromatography with Low-Conductivity Eluents, J. of Chromatography, 186 (1979) pp. 509-519.
Ion Chromatography with Conventional HPLC Instrumentation by J. E. Girard and J. E. Glatz, American Laboratory, Oct. 1981, pp. 26-35.

Primary Examiner—Reinhard J. Eisenzopf
Assistant Examiner—Robert W. Mueller
Attorney, Agent, or Firm—Woodcock Washburn Kurtz Mackiewicz & Norris

[57] ABSTRACT

A high sensitivity conductivity detector for ion chromatography includes an isolated fluid cell and a measuring circuit including an operational amplifier having its input connected to the center tap of a transformer. Feedback from the operational amplifier maintains the center tap at virtual ground potential. The excitation voltage for the transformer is supplied by two operational amplifiers. A thermoelectric semiconductor device maintains the temperature of the sample cell at a constant, ambient temperature.

19 Claims, 7 Drawing Figures

HIGH SENSITIVITY CONDUCTIVITY DETECTOR

BACKGROUND OF THE INVENTION

This invention relates to a high sensitivity conductivity detector, and more particularly, to a detector which can be used in ion chromatography.

Recently, there has been a growing need for reliable techniques for determining mixtures of ions in diluted solutions of solvent. ANION CHROMATOGRAPHY WITH LOW-CONDUCTIVITY ELUENTS by D. T. Gjerde, J. S. Fritz and G. Schmuckler, *J. of Chromatography*, 186 (1979) pp 509–519 describes the ion chromatography (I.C.) technique. Typically, ion chromatography uses a separation column containing an anion exchange resin. The separated anions are detected after passing through a suppressor column to remove background conductance. The disadvantages of use of a suppressor column have been recognized.

Recently, an attempt has been made to perform ion chromatography measurements in a system which does not have a suppressor column.

"ION CHROMATOGRAPHY WITH CONVENTIONAL HPLC INSTRUMENTATION", by J. E. Girard and J. E. Glatz, American Laboratory, October 1981, pp. 26–35 describes a non-suppressed ion chromatography system which includes a Wescan model 213 conductivity detector.

The detection of conductivity changes in such a system is extremely difficult. Typically, a change in conductivity of one part in 30,000 must be measured. Prior art conductivity detectors, such as the CONDUCTOMONITOR TM supplied by Milton Roy Company, have been successfully used in other chromatography measuring techniques, but are not suitable for use in ion chromatography.

One requirement for making measurements of extremely small conductivity changes, is that the temperature of the sample be constant. In other chromatography applications, provision is made for compensating the measurement for temperature changes. The desirability of maintaining the temperature of the sample constant has been recognized, for example, in the aforementioned Wescan instrument in which the sample is heated to a temperature above ambient temperature and maintained at that temperature by control of the heater.

It is an object of the present invention to provide a conductivity detector in which the sample is accurately maintained at a temperature which is approximately ambient temperature, thereby obviating the need for large heat transfers to the sample.

It is another object of the present invention to replace the Wheatstone bridge measurement technique of prior art conductivity detectors with a measurement circuit which is capable of measuring very small changes in conductivity.

It is another object of the present invention to provide a measurement circuit in which a small excitation voltage is applied to the sample cell.

SUMMARY OF THE INVENTION

In accordance with the present invention a detector for measuring the conductivity of a fluid sample with high sensitivity includes a measurement circuit with a transformer having a secondary with a center tap connected to the cell probe and connected to the input of an operational amplifier which maintains the center tap at virtual ground. The operational amplifier produces an output proportional to the conductivity of a sample in the cell. The body of the sample cell is maintained at ground potential. A ring electrode is enclosed within the cell and insulated from it. The fluid sample is continuously supplied through the opening in the ring electrode. An insulated probe extends into contact with the ring electrode.

A small excitation voltage is applied to the cell by driving the two ends of the primary winding of the transformer with driving voltages having equal but opposite alternating excursions with respect to reference potential. Two driving operational amplifiers have their outputs respectively connected to the two ends of the primary winding to produce the driving voltages. This driving arrangement minimizes electrolytic plating and avoids capacitive coupling to the measuring circuit.

Further in accordance with the present invention, a thermoelectric semiconductor device maintains the temperature of the sample cell in a conductivity detector at a constant temperature which is the ambient temperature. The thermoelectric device is controlled in a manner which does not require large heat exchange to and from the sample.

Further in accordance with the invention, a low current, high gain amplifier is used in the measurement circuitry.

The foregoing and other objects, features and advantages of the invention will be better understood from the following more detailed description and appended claims.

SHORT DESCRIPTION OF THE DRAWINGS

DESCRIPTION OF THE PREFERRED EMBODIMENT

Figure 1:
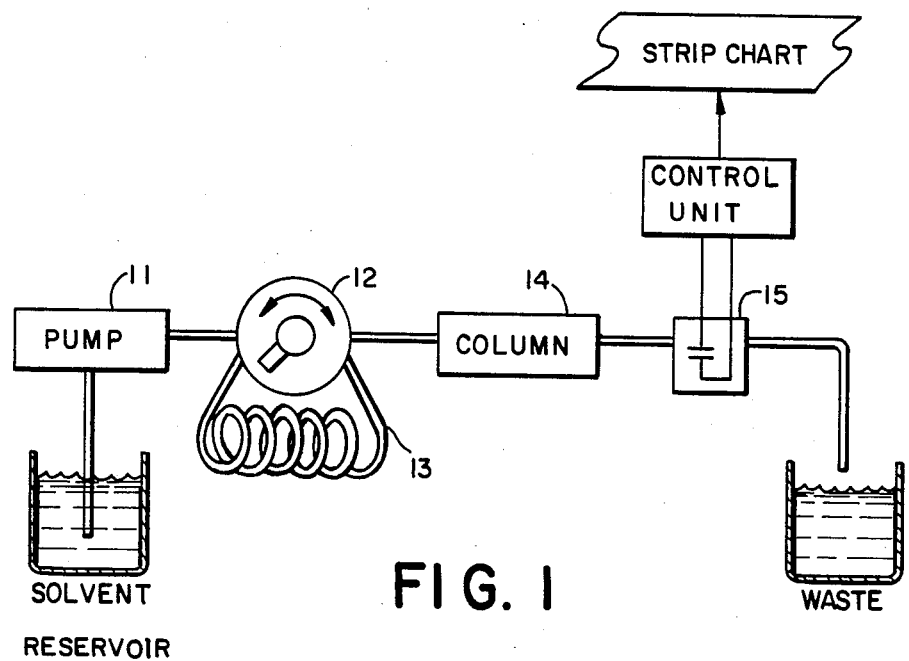
FIG. 1 shows an ion chromatography system in the detector of the present invention may be used.

FIG. 1 shows an ion chromatography system of the type in which the present invention is used. Solvents are delivered by a pump 11 to an injection valve 12 which supplies the solvent to injection loop 13. The solvent is placed under high pressure from a few hundred pounds to several thousand pounds of pressure. The pressurized solvent from the pump passes through the column 14 which is the primary restriction. The column separates the sample. The separated sample passes to the conductivity cell 15 and then it goes to waste. The signal generated is applied to a strip chart recorder or other recording means for analysis.

Figure 2:
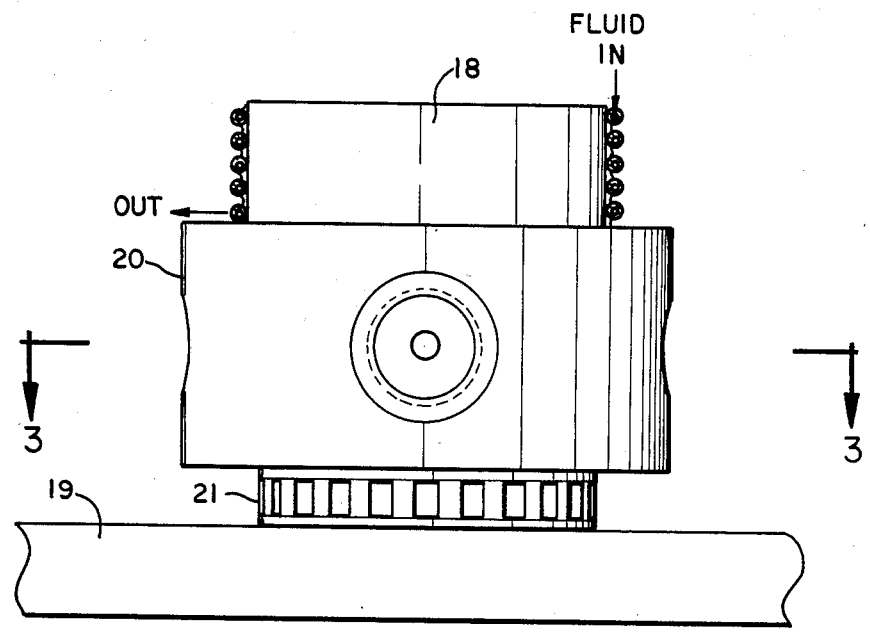
FIG. 2 shows the sample cell, thermoelectric device and heat sink.
Figure 3:
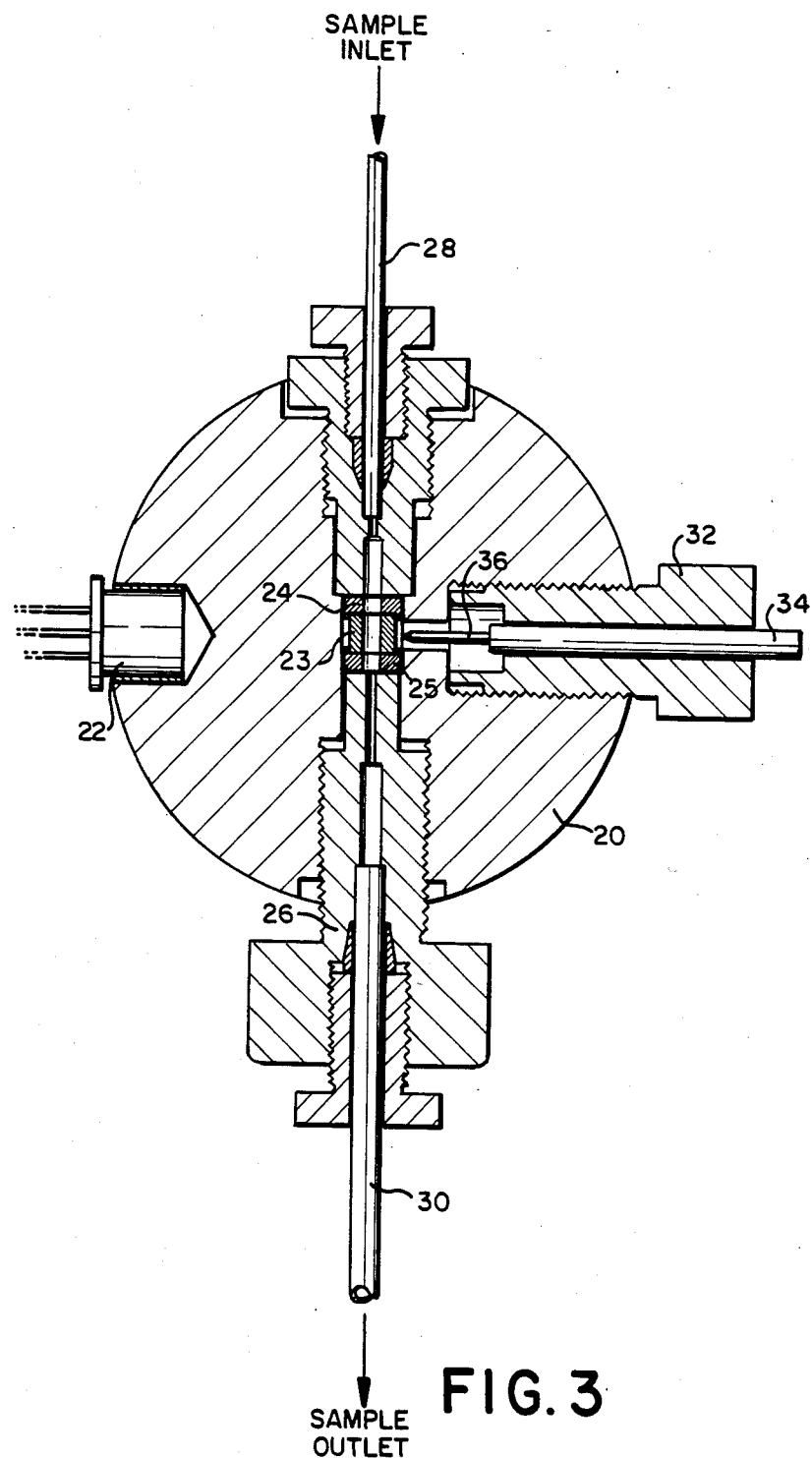
FIG. 3 is a section on the line 3—3 of FIG. 2.

FIGS. 2 and 3 show the fluid cell for holding the samples to be measured. The sample passes through tubing heat exchanger 18 and then into the cell body 20 which is at ground potential. A thermoelectric semiconductor device 21 is in heat exchange relationship with the fluid cell 20. Thermoelectric device 21 transfers heat between the heat sink 19 and the fluid cell body 20.

FIG. 3 shows the temperature sensor 22 for sensing the temperature of the fluid cell body 20. A control circuit responds to the signal from this temperature sensor for controlling the direction of current flow through semiconductor device 21 to heat or cool the cell to maintain the temperature of the fluid sample constant at approximately ambient temperature.

Cell body 20 encloses a stainless steel ring electrode 23 through which the solvent passes. Electrode 23 is insulated in each end of a cavity in cell 20 by washers 24 and 25. These control tolerance by the nut assembly 26 which applies compression to the stack so that it does not leak hydraulically.

A nut 32 presses a spring loaded pin 34 carrying probe 36 which pricks the stainless steel surface of electrode 23.

Solvent enters the cell through sample inlet 28 which is a 1/32" line producing a microliter flow of sample. The solvent passes through an electric field which measures its conductivity and exits through sample outlet 30.

The cell body is grounded and this is very important to the sensitivity of the fluid cell. The only elements at an elevated potential are deep in the middle of the cell, at the sensor electrode. Everything else is grounded. In the prior art, shielding is accomplished by different means. Because the chassis of the fluid cell of the present invention is already at ground, the requirement for guard bands is obviated. The aforementioned CONDUCTOMONITOR TM, for example, required the use of guard bands for shielding. The common electrode was not grounded on the CONDUCTOMONITOR TM. Otherwise, chassis potential differences elsewhere in the equipment would interfere with the measurements because they could broadcast, however weakly, through the solvent or through the pumping to the measurement circuit. A guard electrode was required to shield the circuit from the rest of the plumbing.

Figure 4:
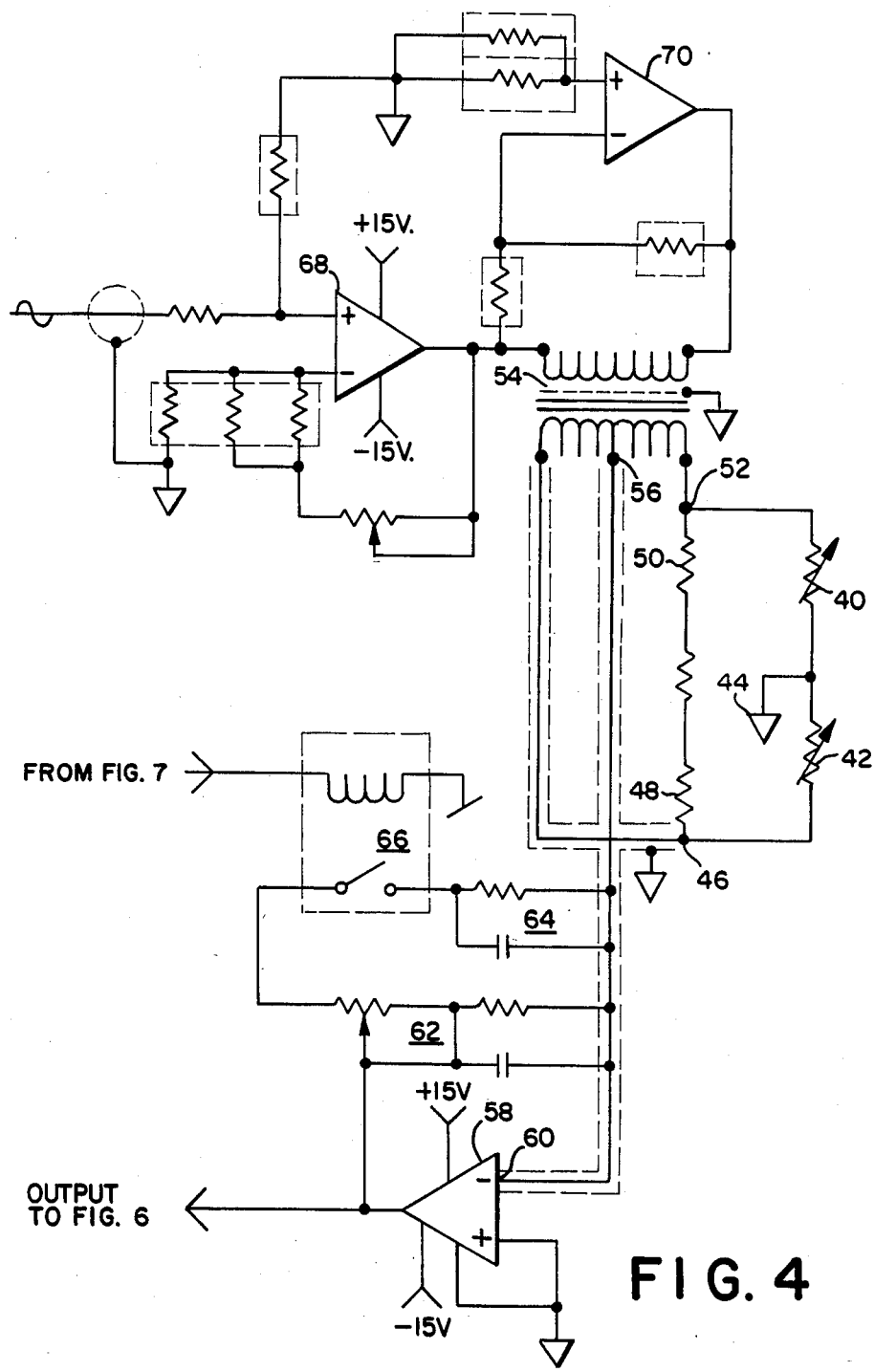
FIG. 4 shows the measurement circuitry of the detector.

Referring to FIG. 4, the electronic circuitry includes a reference path with a reference resistor 40 and a sample path with resistance 42 representing the variable conductivity of the sample. The reference potential applied to the cell is the ground connection at 44. The electrode which is in contact with the sample fluid is connected to a first excitation junction 46. Loading resistors 48 and 50 are respectively connected to the first excitation junction 46 and to a second excitation junction 52.

The excitation potential applied between the sample fluid and reference potential is very small, approximately 50 millivolts. The excitation potential is developed across the secondary winding of a transformer 54. The two ends of the secondary winding are respectively connected to the first excitation junction 46 and the second excitation junction 52. The transformer is resistively loaded to minimize the effects of the source impedance and to linearize the transformer as the cell varies in conductance. The secondary winding of the transformer 54 has a center tap 56 which is connected to input 60 of operational amplifier 58.

Operational amplifier 58 maintains the center tap at virtual ground by feedback. As a result, the current flowing to the inverting input 60 is directly proportional to the conductance of the sample fluid. Operational amplifier 58 generates a current which is equal to, but opposite from, the current supplied to the inverting input 60. The current generated by amplifier 58 is coupled through the path 62 or the path 64, depending upon the range setting as determined by the range relay 66, to cancel the current which is proportional to sample fluid conductivity. As a result, the voltage developed at the output of operational amplifier 58 is proportional to the conductivity of the sample fluid.

The transformer drive for the fluid cell provides isolation in the grounding of the detector thereby providing improved sensitivity. The return currents from the cell measurement are very important because very small differences in ground potentials at the fluid cell appear as common mode voltages to those used to excite the fluid cell. The fluid cell must be driven with a precision voltage, and anything that contributes to upsetting that makes the measurement very noisy or not repeatable. Being able to isolate the drive from the measurement and making the measurement at ground potential in accordance with the present invention is very important.

The excitation voltage applied to the primary winding of transformer 54 is generated by second and third driving operational amplifiers 68 and 70. The outputs of these operational amplifiers are respectively connected to the two ends of the primary winding of transformer 54. An alternating excitation voltage is applied to the inputs of the amplifiers so that the amplifiers drive the ends of the primary winding with equal alternating excursions with respect to reference potential.

The fluid cell should be driven with equal positive and negative potentials of a sine wave. If they are not equal, electrolytical plating will take place. Metal ionizes onto the electrode surfaces and that will poison the detector because it no long has a good surface conductivity.

If the transformer is driven with one side of the primary winding at ground potential, the parasitic capacitance of the transformer, which is equal on both sides of the transformer, results in a large 90° out of phase signal. This results in capacitive coupling of the drive voltage to the secondary side of the cell input. To avoid this, a balanced drive is required. Both sides of the transformer must be driven at the same rate, but with opposite polarities so that the feed through of this parasitic capacitance is cancelled. Operational amplifiers 68 and 70 and associated circuitry, provide the desired driving voltage.

Figure 5:
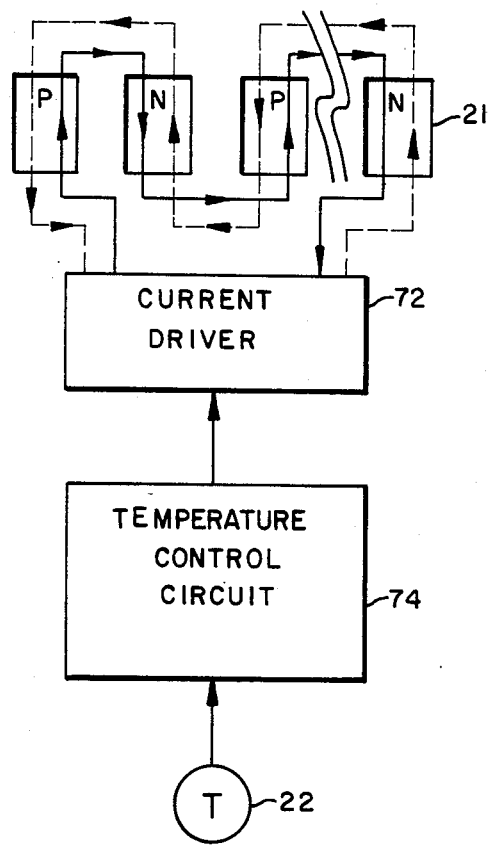
FIG. 5 is a block diagram of the temperature control for the thermoelectric device.

Referring to FIG. 5, the thermoelectric temperature control device and its control circuit are shown. The thermoelectric device 21 has alternating P and N semiconductor elements. Current is driven through these elements in the direction shown by the solid line with arrows or alternatively it is driven in the direction indicated by the dashed line with arrows. When current goes through a P element from bottom to top, heat is transferred in one direction. Current flow through an N element produces heat flow in the opposite direction. Therefore, when current flow is in one direction, heat transfer is from the bottom to the top of the device, resulting in heating of the fluid cell. When current flows is in the opposite direction, the fluid cell is cooled.

A current drive 72 and a temperature control circuit 74 control the direction and amount of current flowing through the thermoelectric device 21. Temperature control circuit 74 responds to the signal from the temperature sensor 22. Control circuit 74 generates a set point which closely approximates ambient temperature.

Temperature from the sensor 22 is compared to this set point and an appropriate control signal is generated.

Figure 6:
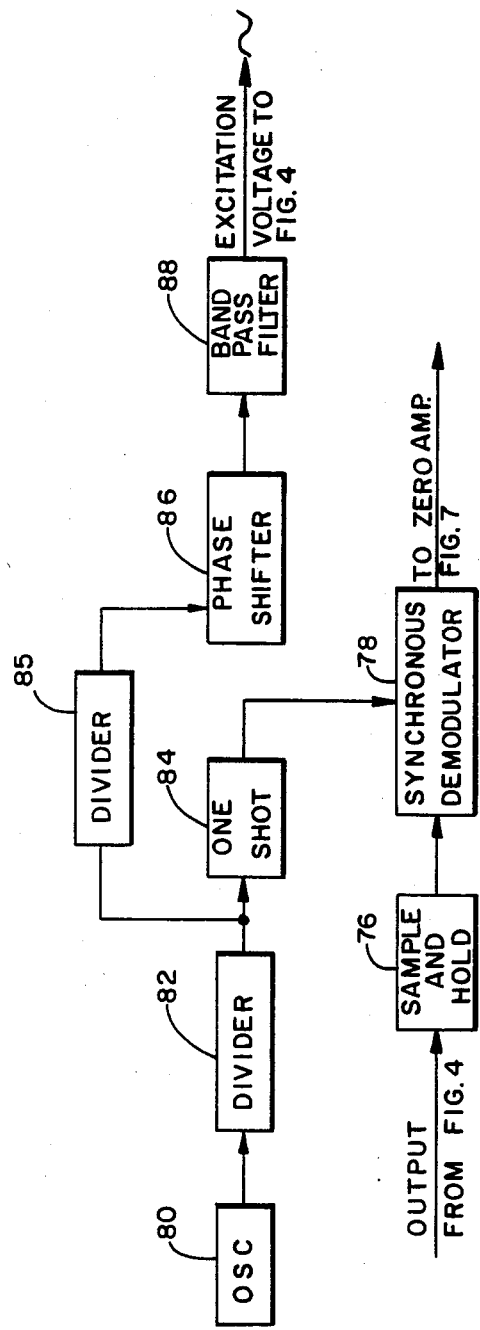
FIG. 6 is a block diagram showing the synchronous detector driven from the same source which produces the excitation voltage for the measurement circuit.

FIG. 6 shows the signal processing circuitry and the circuitry for generating the excitation voltage. The output of the operation amplifier 58 in FIG. 4 is an AC signal whose magnitude is proportional to the conductance of the fluid sample. This must be converted to a DC signal whose magnitude is proportional to conductance. In order to do this, the operational amplifier output is applied to a sample and hold circuit. Synchronous demodulator 78 includes a switch amplifier which converts the input signal, with a gain of ten, to a DC output.

In order to produce an excitation voltage, an oscillator 80 drives a digital divider 82 to produce a 50% duty cycle square wave. A one shot 84 produces the signal which drives the synchronous demodulator 78. The same signal is used to generate the excitation voltage for the fluid cell so that the output voltage is properly sampled at the peak of the output of the operational amplifier 60. This assumes that the output representing conductance is purely resistive. If there are any capacitive effects, they should not be measured. By always measuring at a constant phase relative to the excitation voltage, the circuit is immune to changes in the dielectric constant of the sample being measured. Divider 85 and phase shifter 86 provide means for adjusting the phase of the excitation voltage relative to the sampling point of the synchronous demodulator. If it is desired to measure the dielectric constant of the sample, all that is required is to shift phase by 90°.

Bandpass and low pass filters 88 remove the d.c. component of the square wave and the harmonics of the square wave, so that only the fundamental is present, which is 2 kilohertz in an exemplary embodiment.

Figure 7:
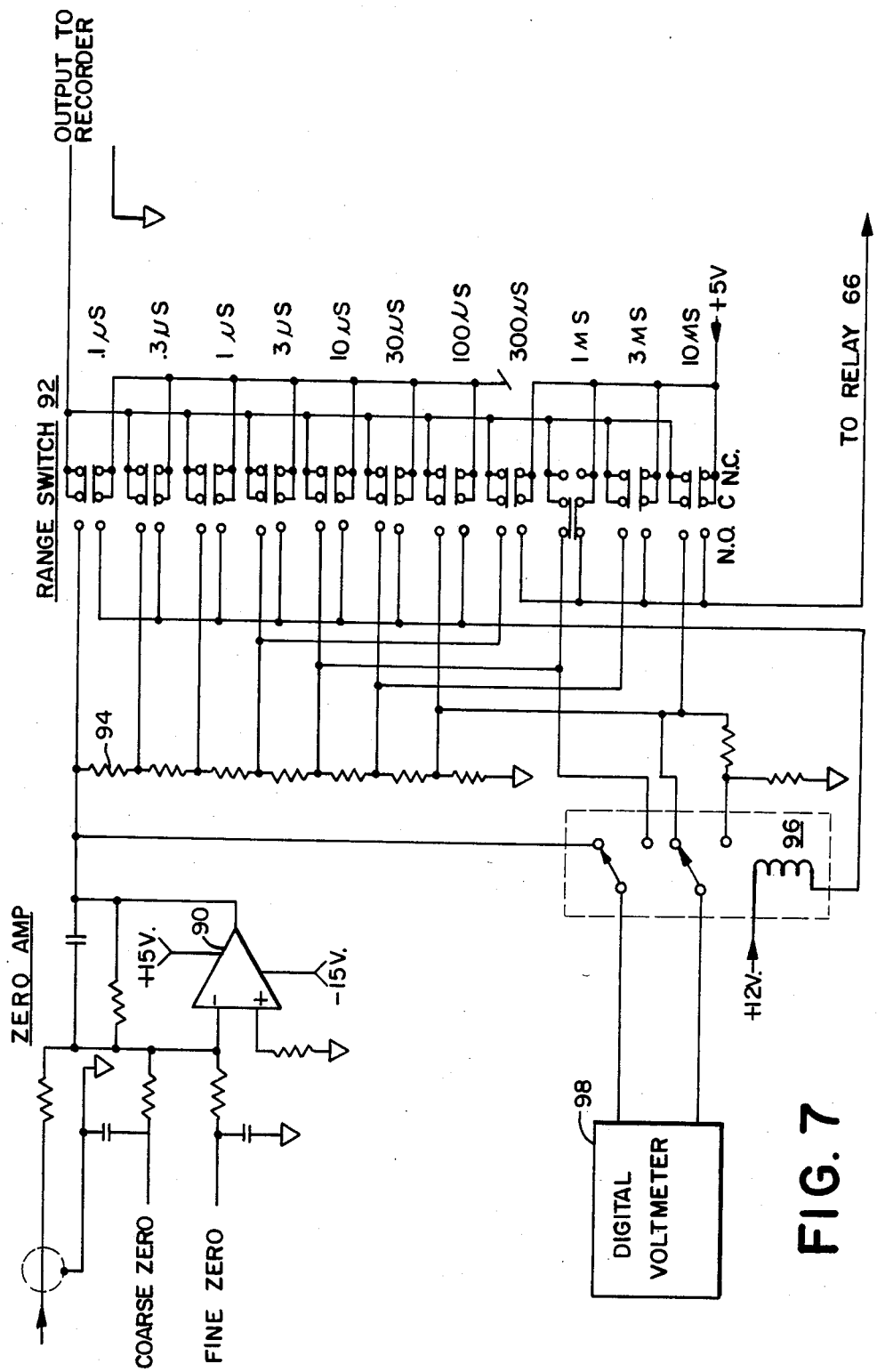
FIG. 7 shows the zero amplifier and the range changing switch.

FIG. 7 shows the zero amplifier which provides an electronic offset and the range changing switch. The converted output of the synchronous demodulator is a d.c. voltage that is proportional to the conductance of the sample and the background conductance. It is necessary to remove the background conductance from the measurement so that small changes in the conductance can be observed, and/or recorded. This is done with the zero amplifier 90 which is a differential amplifier having an attenuator network connected to its input. The amplifier 90 produces an output which is the difference between the input voltage from the synchronous demodulator and an offset voltage which is manually set and applied to amplifier 90 through the attenuator network.

Because of range changes at the front end of the detector, there are two effective zero suppression ranges. Relay 66 in FIG. 4 switches the amplifier 58 between these two ranges. In the microsiemens range, 150 microsiemens of offset suppression can be applied to the zero amplifier 90 in FIG. 7. In the millisiemens range, 15 millisiemens of background suppression can be applied. In this way, 150,000% of zero suppression is provided.

Range switch 92 has ganged double pole, double throw, switches which selectively insert attenuating resistors between the output of zero amplifier 90 and the output of the detector system. One pole is used to connect the signal to the recorder. For example, in the 0.1 microsiemen range, the top pole of the top switch connects the signal unattenuated to the recorder. In the 0.3 microsiemen range, the top pole of the second switch connects the signal through the resistor 94 to the recorder. Range switch 92 is an interlocking switch so that when one range switch is manually engaged, another is disengaged.

The other pole of the range switch is used to control relay 66. When one of the switches of the millisiemens group in range switch 92 is actuated, +5 volts is applied to relay 66 in FIG. 4 to actuate that relay to change the range of the operational amplifier 58.

Relay 96 is actuated when one of the microsiemen range switches in range switch 92 are closed. This changes the scale of the signal applied to a digital voltmeter 98 which is used for diagnostic display.

While a particular embodiment of the invention has been shown and described, various modifications are within the true spirit and scope of the invention. The appended claims are, therefore, intended to cover all such modifications.

What is claimed is:

1. A detector for measuring the conductivity of a fluid sample with a high sensitivity comprising:
   a cell for holding the sample to be measured, said cell being maintained at a reference potential;
   an electrode in electrical contact with said fluid in said cell;
   a transformer having a primary winding having two ends and a center tap secondary winding, an excitation voltage being applied to said primary winding, the secondary winding of said transformer being connected between said electrode and said reference voltage;
   an operational amplifier having an input connected to the center tap of said transformer, said operational amplifier responding to current flow to maintain said center tap at virtual reference potential, said operational amplifier producing an output proportional to the conductivity of said sample in said cell; and
   a loading resistor connected between a first and second excitation junctions;
   wherein said electrode is connected to said first excitation junction and said secondary winding of said transformer is connected between said first and second excitation junctions.

2. The detector recited in claim 1 wherein said cell includes
   a cell body maintained at reference potential and wherein
   said electrode further comprises:
   a ring electrode enclosed within said cell body and insulated therefrom, said fluid sample being continuously supplied through the opening in said ring electrode; and
   an insulated probe extending into contact with said ring electrode.

3. The detector recited in claim 2 wherein the two ends of the primary winding of said transformer are driven with driving voltages having equal but opposite alternating excursions with respect to reference potential.

4. The detector recited in claim 3 further comprising:
   two driving operational amplifiers having outputs respectively connected to said two ends of said primary winding and producing said driving voltages.

5. The detector recited in claim 1 wherein the two ends of the primary winding of said transformer are driven with driving voltages having equal but opposite alternating excursions with respect to reference potential.

6. The detector recited in claim 5 further comprising:
two driving operational amplifiers having outputs respectively connected to said two ends of said primary winding and producing said driving voltages.

7. The detector recited in claim 1 further comprising:
second and third operational amplifiers having outputs respectively connected to the two ends of the primary winding of said transformer, an alternating excitation voltage being applied to the input of said second and third operational amplifiers, said second and third operational amplifiers driving the two ends of said primary winding with equal alternating excursions with respect to reference potential.

8. The detector recited in claim 1 further comprising:
two feedback paths between the output of said operational amplifier and the input; and
a range changing relay, switching said feedback paths to change the range of said operational amplifier.

9. The detector recited in claim 1 further comprising:
a thermoelectric semiconductor device in heat exchange relationship with said cell;
a temperature sensor producing a signal representing the temperature of said fluid in said cell; and
a control circuit responsive to said signal for controlling the direction of current flow through said semiconductor device to heat or cool said cell, whereby the temperature of said fluid sample is maintained constant at approximately ambient temperature.

10. The detector recited in claim 9 wherein said cell includes
a cell body maintained at reference potential and wherein
said electrode further comprises
a ring electrode enclosed within said cell body and insulated therefrom, said fluid sample being continuously supplied through the opening in said ring electrode; and
an insulated probe extending into contact with said ring electrode.

11. The detector recited in claim 9 further comprising:
second and third operational amplifiers having outputs respectively connected to the two ends of the primary winding of said transformer, an alternating excitation voltage being applied to the input of said second and third operational amplifiers, said second and third operational amplifiers driving the two ends of the primary winding with equal alternating excursions with respect to reference potential.

12. The detector recited in claim 9 further comprising:
a synchronous demodulator for detecting a peak output of said operational amplifier;
a source of said excitation voltage;
said synchronous demodulator being driven by said source, said source further generating said excitation voltage for said cell;
wherein said output voltage is sampled at the peak of the output of said operational amplifier.

13. The detector recited in claim 9 in an ion exchange chromatography system for measuring the conductivity of effluent from a column in said ion exchange chromatography system.

14. The detector recited in claim 9 wherein said thermoelectric device comprises:
alternating P and N semiconductor elements; and
means for supplying current through said elements in one direction to transfer heat across said device in one direction and for supplying current through said device in the other direction to transfer heat across said device in the other direction.

15. The detector recited in claim 1 in an ion exchange chromatography system for measuring the conductivity of effluent from a column in said ion exchange chromatography system.

16. The detector recited in claim 1 wherein said cell comprises:
a cell body maintained at reference potential;
a ring electrode in a cavity in said body and insulated therefrom; and
sample inlet and exit ports for transporting fluid through said ring electrode.

17. The detector recited in claim 1 further comprising:
a synchronous demodulator for detecting a peak output of said operational amplifier;
a source of said excitation voltage;
said synchronous demodulator being driven by said source, said source further generating said excitation voltage for said cell;
wherein said output voltage is sampled at the peak output of said operational amplifier.

18. The detector recited in claim 17 further comprising:
a zero amplifier connected to an output of said synchronous demodulator;
an attenuator network connected to an input of said zero amplifier; and
means for selectively applying different offset voltages to said zero amplifier input to effect different electronic offsets.

19. The detector recited in claim 1 further comprising:
a range switch connected to the output of said operational amplifier, said range switch having ganged interlocked switches;
a plurality of attenuating resistors, wherein the interlocked switches switch selectively, connect attenuating resistors to the output of said operational amplifier.

* * * * *